(12) United States Patent
Rool et al.

(10) Patent No.: US 10,570,089 B2
(45) Date of Patent: Feb. 25, 2020

(54) PROCESS FOR PREPARING AMINOTHIOL ESTER COMPOUNDS AND SALTS THEREOF

(71) Applicant: ADVANCED BIODESIGN, Saint Priest (FR)

(72) Inventors: Patrice Rool, Riom (FR); Benoit De Carne-Carnavalet, Riom (FR)

(73) Assignee: ADVANCED BIODESIGN, Saint Priest (FR)

( * ) Notice: Subject to any disclaimer, the term of this patent is extended or adjusted under 35 U.S.C. 154(b) by 0 days.

(21) Appl. No.: 16/077,653

(22) PCT Filed: Feb. 16, 2017

(86) PCT No.: PCT/EP2017/053457
§ 371 (c)(1),
(2) Date: Aug. 13, 2018

(87) PCT Pub. No.: WO2017/140754
PCT Pub. Date: Aug. 24, 2017

(65) Prior Publication Data
US 2019/0047948 A1    Feb. 14, 2019

(30) Foreign Application Priority Data
Feb. 17, 2016   (FR) ..................................... 16 51283

(51) Int. Cl.
*C07C 319/14*    (2006.01)
*C07C 319/28*    (2006.01)
*C07C 327/30*    (2006.01)

(52) U.S. Cl.
CPC .......... *C07C 319/14* (2013.01); *C07C 327/30* (2013.01); *C07C 319/28* (2013.01)

(58) Field of Classification Search
CPC ... C07C 319/28; C07C 319/24; C07C 327/30; C07C 319/14
See application file for complete search history.

(56) References Cited

U.S. PATENT DOCUMENTS

2003/0181443 A1    9/2003    Fournet

OTHER PUBLICATIONS

International Search Report dated Apr. 24, 2017 during the prosecution of International Application No. PCT/EP2017/053457.

Preliminary Search Report dated Oct. 5, 2016 during the prosecution of French Application No. FR1651283.

Quash Get Al: "Aldehyde dehydrogenase inhibitors: @a,@b-Acetylenic N-substituted aminothiolesters are reversible growth inhibitors of normal epithelial but irreversible apoptogens for cancer epithelial cells from human prostate in culture", European Journal of Medicinal Chemistry, Editions Scientifique Elsevier, Paris, FR, vol. 43, No. 5, May 1, 2008 (May 1, 2008), pp. 906-916, XP022639683; cited in ISR & FR Preliminary Search Report.

Naseem Sadia et al: "Photo-isomerization upshifts the pKaof the Photoactive Yellow Protein chromophore to contribute to photocycle propagation", Journal of Photochemistry and Photobiology, A: Chemistry, vol. 270, 2013, pp. 43-52, XP028704667 cited in ISR & FR Preliminary Search Report.

Benjamin Koeppe et al: "Solvent and H/D Isotope Effects on the Proton Transfer Pathways in Heteroconjugated Hydrogen-Bonded Phenol-Carboxylic Acid Anions Observed by Combined UV-vis and NMR Spectroscopy", Journal of the American Chemical Society, vol. 135, No. 20, May 22, 2013 (May 22, 2013), pp. 7553-7566, XP055307350; cited in ISR & FR Preliminary Search Report.

Benjamin Koeppe et al: "Solvent and H/D Isotope Effects on the Proton Transfer Pathways in Heteroconjugated Hydrogen-Bonded Phenol-Carboxylic Acid Anions Observed by Combined UV-vis and NMR Spectroscopy", extract Internet, 2013, XP55307400.

*Primary Examiner* — Rebecca L Anderson
(74) *Attorney, Agent, or Firm* — Troutman Sanders LLP

(57) ABSTRACT

A process for preparing aminothiol ester compounds and salts thereof. The present invention relates to a process for preparing compounds of formula (I), (I) comprising the following steps: a) reacting a compound of formula (II) with an inorganic acid or an organic acid, (II) b) reacting the compound obtained in step a) with a base; c) reacting the compound obtained in step b) with $CO_2$; d) reacting the compound obtained in step c) with an alkyl chloroformate, a reagent capable of forming, with the compound obtained in step c), an acid halide, or a reagent capable of forming, with the compound obtained in step c), a mixed anhydride; e) reacting the compound obtained in step d) with an SMe anion precursor compound.

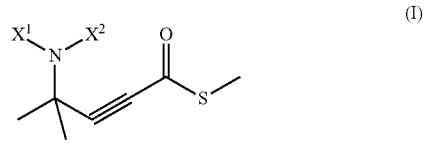

(I)

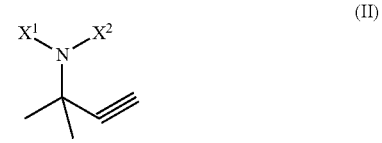

(II)

19 Claims, No Drawings

PROCESS FOR PREPARING AMINOTHIOL ESTER COMPOUNDS AND SALTS THEREOF

CROSS-REFERENCE TO RELATED APPLICATIONS

This is a U.S. national phase application under 35 U.S.C. § 371 of International Patent Application No. PCT/EP2017/053457, filed Feb. 16, 2017 and claims benefit of priority to French Patent Application No. 1651283, filed Feb. 17, 2016.

FIELD OF THE INVENTION

The present invention relates to a method for preparing aminothiol ester compounds and salts of the compounds.

BACKGROUND

A method for the preparation of such products is described, in particular, in US2003/0181443.

However, the first step of this method involves 3-chloro-3-methylbut-1-yne the supply of which may be uncertain. In addition, the purity of the commercial product is variable and may have an impact on the remainder of the reaction chain, particularly in terms of yield. Moreover, the purification steps for this first step appear to be difficult to transpose to a large scale, while the product of this first step tends making the purification steps all the more difficult.

The second step of this method uses carbon oxysulfide (COS) which is a toxic product and the supply of which is uncertain depending on the country.

It is therefore necessary to provide a method to solve the disadvantages of the prior art.

SUMMARY

An object of the present invention is to provide a method for preparing aminothiol ester compounds and their salts, while limiting the implementation of toxic products, in particular by not using COS.

Another object of the invention is to provide a method employing reagents that do not present a problem of supply, and in particular a method that does not use commercial 3-chloro-3-methylbut-1-yne.

Another objective of the invention is to provide a method for which the products and reagents are not likely to sublimate during the various steps of the method and, in particular, during purification.

Other objectives will become apparent upon reading the description which follows.

These objectives are fulfilled by the present invention which proposes a method for the preparation of compounds of formula (I)

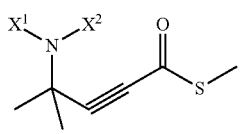

(I)

in which $X^1$ and $X^2$, which are identical or different, are chosen from $C_1$ to $C_7$ alkyls, phenyl, benzyl, or $X^1$ and $X^2$ form with the nitrogen atom which carries them, a heterocycle, in particular piperidine or morpholine, wherein the method comprises the following steps:

a) reaction of a compound of formula (II) with an inorganic acid or an organic acid

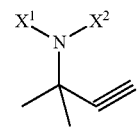

(II)

b) reaction of the compound obtained in step a) with a base;
c) reaction of the compound obtained in step b) with $CO_2$;
d) reaction of the compound obtained in stage c) with an alkyl chloroformate, i.e. a reagent that is likely to form, with the compound obtained in stage c), an acid halide or a reagent likely to form, with the compound obtained in step c), a mixed anhydride;
e) reaction of the compound obtained in step d) with an $SMe^-$ anion precursor compound.

The steps of the method may be carried out without purification and without isolating the intermediate products. As explained below, intermediate purifications may be implemented, in particular to improve the yield of the next step.

In the context of the present invention, a $C_1$-$C_7$ alkyl group is understood to mean a linear or branched hydrocarbon aliphatic group comprising, unless stated otherwise, from 1 to 7 carbon atoms. Alkyl groups comprising from 1 to 3 carbon atoms are preferably targeted. By "branched" is meant that one or more alkyl groups, for example methyl, ethyl or propyl are attached to the linear alkyl chain. Examples of the alkyl group include methyl, ethyl, n-propyl, i-propyl, n-butyl, t-butyl, 2,2-dimethylbutyl, n-pentyl, n-hexyl, n-heptyl, especially methyl.

In particular, the compounds of formula (I) are compounds for which $X^1$ and $X^2$, which are identical or different, are chosen from methyl, phenyl and benzyl, wherein at least either $X^1$ or $X^2$ is methyl, or $X^1$ and $X^2$ form with the nitrogen atom carrying them, a piperidine or morpholine cycle.

Preferably, the compounds of formula (1) are chosen from:
S-methyl 4-methyl-4-(piperidin-1-yl)pent-2-ynethioate;
S-methyl 4-[benzyl(methyl)amino]-4-methylpent-2-ynethioate;
S-methyl 4-methyl-4-[methyl(phenyl)amino]pent-2-ynethioate;
S-methyl 4-methyl-4-(morpholin-4-yl)pent-2-ynethioate;
S-methyl 4-(dimethylamino)-4-methylpent-2-ynethioate;
S-methyl 4-(diheptylamino)-4-methyl-pent-2-ynethioate; and/or
S-methyl 4-[heptyl(methyl)amino]-4-methyl-pent-2-ynethioate.

Preferably, the compound of formula (I) is S-methyl 4-(dimethylamino)-4-methylpent-2-ynethioate.

The compound of formula (II) according to the invention, optionally in salified form, may be obtained by any method known to those skilled in the art. In a particular embodiment, the compound of formula (II) may be obtained by reaction of 3-chloro-3-methylbut-1-yne with a compound of formula $X^1X^2NH$. Such reactions are described, in particular, in Hennion et al., JACS, 1960, 4908-4912, incorporated herein by reference. Preferably in this embodiment, the compound of formula (II) is obtained by a step a1) of reaction of 3-chloro-3-methylbut-1-yne with $X^1X^2NH$ in an aqueous medium. Preferably, this step a1) is carried out with 1 to 3 equivalents of $X^1X^2NH$ relative to the number of moles of 3-chloro-3-methylbut-1-yne. Preferably, step a1) is carried out at a temperature between 0 and 50° C., preferably between 10 and 40° C., preferably at room temperature, i.e. at a temperature between 20 and 25° C. The compound obtained in step a1) may be purified before its implementation in step a). The purification may, in particular, consist of one or more filtrations, for example in 1 filtration or in a succession of 2 to 10 filtrations, preferably in a succession of 2 to 5 filtrations, for example in 4 filtrations. In this embodiment, 3-chloro-3-methylbut-1-yne may be commercially available or may be obtained by step a0) by the reaction of 2-methylbut-3-yn-2-ol with a mineral acid, preferably hydrochloric acid, in the presence of a copper catalyst. Preferably, in step a0), the acid is used in an amount of 3 to 10, preferably 5, equivalents relative to the number of moles of 2-methylbut-3-yn2-ol. Preferably, step a0) is carried out in the presence of calcium chloride (for example $CaCl_2$, copper chloride (for example $CuCl_2$ or CuCl, preferably $CuCl_2$ and Cu. Preferably in step a0), calcium chloride is used in a proportion of 0.1 to 1, preferably 0.2 to 0.7, equivalents relative to the number of moles of 2-methylbut-3-yn-2-ol. Preferably in step a0), the copper chloride is used in a proportion of 0.1 to 1, preferably 0.2 to 0.7, equivalents relative to the number of moles of 2-methylbut-3 yn-2-ol. Preferably, in step a0), the Cu is used in a catalytic amount, in particular in a proportion of 0.005 to 0.1, preferably of 0.007 to 0.05, equivalents relative to the number of moles of 2-methylbut-3-yn-2-ol. Preferably, step a0) is carried out at a temperature between −78° C. and 10° C., preferably between −50° C. and 0° C.

In another embodiment of the invention, the compound of formula (II) may be obtained by reaction between an acetate or a phosphate of the 2-methyl-3-butyn-2-ol and a compound of formula $NHX^1X^2$ in the presence of a catalyst, especially with copper. Such a reaction is, in particular, described in J. Org. Chem. 1994, 59, 2282-2284. In this embodiment, the starting compound is a compound of formula $H-C\equiv C(Me)_2$-OR, wherein R represents $OP(O)(OEt)_2$ or OAc. Preferably, the reaction is carried out in the presence of copper chloride, on particular CuCl.

In another embodiment, the compound of formula (II) may be obtained by dimethylation of 1,1-dimethylpropargylamine (commercial), in particular by formic acid in the presence of aqueous paraformal-dehyde, as described in J. Org. Chem, 1957, 22, 840-843.

Step a) is preferably carried out in the presence of a solvent, wherein the solvent is chosen from solvents which solubilize the inorganic acid or the organic acid but which do not solubilize the product formed during step a). For example, the solvent may be chosen from alcohols, in particular methanol, isopropanol, dioxane and ether. Preferably, the solvent is dioxane.

Preferably, in step a), the inorganic or organic acid is introduced in solution in the solvent, wherein the solution preferably comprises from 1 to 3 molar equivalents of acid.

Preferably, in step a), the inorganic acid is selected from hydrochloric acid, phosphoric acid, nitric acid, sulfuric acid, preferably hydrochloric acid.

Preferably, in step a), the organic acid is selected from carboxylic acids, sulfonic acids.

Preferably, in step a), the acid is an inorganic acid and is preferably hydrochloric acid.

Preferably, step a) is carried out at a temperature between 0 and 50° C., preferably between 0 and 20° C.

The salt obtained in step a) may be purified, in particular by filtration and then recrystallization, in particular under the conditions defined by Hennion et al., J. Am. Chem. Soc. 1957, 79, 2142-2145. Preferably, the salt is purified by recrystallization, preferably from a mixture of ester and alcohol, in particular in a mixture of ethyl acetate and ethanol.

Advantageously, step a) makes it possible to obtain a product in the form of a salt which does not sublime, thus making it possible to overcome the disadvantages of the prior art.

The base used in step b) may be chosen from the bases known to those skilled in the art to deprotonate a true alkyne. Preferably, the base is chosen from bases having a pKa greater than 25. Preferably, the base used in step b) is chosen from lithium or magnesium bases, preferably the base is chosen from butyllithium, or hexyllithium. Preferably the base is butyllithium and, more particularly, n-butyllithium.

Preferably, the amount of base used is between 1.5 and 4, preferably between 1.5 and 2.5, equivalents relative to the number of moles of salt obtained in step a). Preferably, when the compound of formula (II) according to the invention is used as such, the amount of base used is 1.5 equivalents, while when the compound of formula (II) according to the invention is used in salt form, the base amount used is 2.5 equivalents.

The addition of the base is an exothermic reaction. It is therefore preferable to add the base at a temperature below 0° C., preferably at a temperature between −78 and 0° C., preferably between −78 and −50° C., while, after addition, the temperature can no longer be controlled and the reaction medium is preferably allowed to rise to 0° C.

Step b) may be carried out in the presence of a solvent, especially chosen from ethers, in particular chosen from tetrahydrofuran, methyltetrahydrofuran, diethyl ether, dioxane, diisopropyl ether and methyl tert-butyl ether. Preferably, the solvent is tetrahydrofuran (THF).

Preferably, the addition of $CO_2$ to step c) may be done by bubbling $CO_2$ into the reaction medium or by producing $CO_2$ gas in situ by adding dry ice to the reaction medium. The $CO_2$ is preferably used in large excess, in particular, in the case where dry ice is used for the in-situ production of $CO_2$ gas, wherein the amount of dry ice added is between 1 and 50 times the weight of the amine compound obtained in step b).

The addition of $CO_2$ in step c) (via bubbling or dry ice) is accompanied by an increase in temperature. Thus, and preferably, the $CO_2$ is added at a temperature below 0° C., preferably at a temperature between −78 and 0° C., preferably between −78 and −50° C., while, after adding, the temperature can no longer be controlled and the reaction medium is preferably allowed to rise to 0° C.

Advantageously, the product obtained in step c) may be purified by any method known to those skilled in the art. The purification step may, in particular, consist of adding methanol to trap the base, adding inorganic acid, especially HCl, to isolate the product in salt form or adding water or methanol to trap the base, then adding a solvent allowing the precipitation of the product so formed, wherein the solvent is, in particular, chosen from acetonitrile, or methanol, preferably acetonitrile, and the filtration of the reaction medium so obtained. In this purification step, the product of step c) is in the retenta of the filtration. Another purification method is to form a hydrochloride after quenching the base by addition of methanol. These methods are well known to those skilled in the art.

The objective of step d) is to activate the acid function of the compound obtained in step c).

Preferably, the alkyl chloroformate implemented in step d) has an alkyl of 1 to 6 carbon atoms, which may comprise at least one double bond. Preferably, it is a methyl, ethyl, isoprenyl, tert-butyl or isobutyl chloroformate, preferably isobutyl chloroformate.

Those skilled in the art are able to determine the reagents capable of forming a mixed anhydride or an acid halide with the compound obtained in step c).

Preferably, the reagents capable of forming a mixed anhydride with the compound obtained in step c) are chosen from acid chlorides, for example pivaloyl chloride.

Preferably, the reagents capable of forming an acid halide with the compound obtained in stage c) are chosen from the reactants which may form, with the compound obtained in stage c), an acid chloride or bromide, wherein, for example, they are chosen from among $SOCl_2$, $COCl_2$, $PCl_3$, $PCl_5$, $PBr_3$ or $PPh_3Br_2$.

The amount of alkyl chloroformate, of reagent likely to form a mixed anhydride or an acid halide with the compound obtained in step a) and implemented in step d) may be between 1 and 3, preferably between 1 and 2, equivalents relative to the number of moles of the compound obtained in step c).

Preferably step d) is carried out with an alkyl chloroformate.

Preferably, step d) is carried out at a temperature between −78° C. and 50° C., preferably between −0 and 25° C.

If the product of step c) is not purified then no additional solvent is added in step d). In the opposite case, step d) is preferably carried out in the presence of a solvent chosen in particular from those described for step b), preferably THF.

Preferably, in the context of the present invention, the SMe⁻ anion precursor compounds are compounds capable, particularly in the reaction medium or in the presence of a base, of generating the SMe⁻ anion. These compounds are in particular chosen from the salts of formula XSMe in which X represents an alkali metal or alkaline earth metal, for example Na, methyl mercaptan, or $(SMe)_2$. When methyl mercaptan or $(SMe)_2$ are used, it is necessary to add a base to the reaction medium, in particular a base whose pKa is greater than 14, for example sodium, alcoholate (e.g. sodium alkoxide, for example sodium ethanolate), ethylate, methylate, sodium tert-butoxide, etc. Preferably, in step e), the SMe anion precursor compound is chosen from the compounds of formula XSMe in which X represents an alkali metal or alkaline earth metal, preferably NaSMe. In step e), NaSMe may be used as a powder or as a solution in water. The SMe⁻ anion precursor compound is used, in particular so as to obtain from 1 to 3, preferably from 1 to 2 equivalents of SMe⁻ anions relative to the number of moles of the compound obtained in step d).

Preferably, step e) is carried out at a temperature between 0 and 50° C., preferably at room temperature (between 20 and 25° C.).

Preferably, the method of the invention comprises the following steps:
a0) optionally a step a0), reaction of 2-methylbut-3-yn-2-ol with an inorganic acid, especially hydrochloric acid in the presence of a copper catalyst;
a1) optionally, in the case where step a0) has been carried out, reaction of 3-chloro-3-methylbut-1-yne, where appropriate obtained in step a0) with $X^1X^2NH$ in an aqueous medium;

a) reaction of a compound of formula (II) obtained in step a1) where appropriate, or commercial with an inorganic acid, preferably HCl

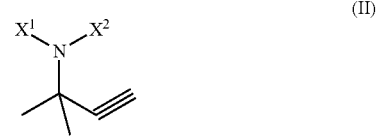

(II)

b) reaction of the compound obtained in step a) with a base, preferably alkyl lithium, preferably butyllithium and more particularly n-butyllithium;
c) reaction of the compound obtained in step b) with $CO_2$;
d) reaction of the compound obtained in step c) with an alkyl chloroformate, preferably isobutyl chloroformate;
e) reaction of the compound obtained in step d) with SMeNa.

The particular and preferred characteristics of the various steps described above, in particular temperature, quantity of reagents, etc., also apply to the description of this preferred process.

The present invention also relates to the preparation of a salt of a compound of formula (I) comprising the steps of:
i) preparation of the compound of formula (I) according to the method of the invention;
ii) reaction of the compound obtained in step i) with the acid corresponding to the desired salt.

Preferably, step ii) is carried out in the presence of alcohol or a mixture of alcohol and ether. The alcohol is preferably chosen from ethanol, methanol and isopropanol. Preferably, the ether is chosen from tetrahydrofuran, methyltetrahydrofuran, diethyl ether, dioxane, diiso-propyl ether, methyl tert-butyl ether and ethyl acetate. Preferably, the solvent is tetrahydrofuran (THF). Preferably, the ether corresponds to the alcohol used. Preferably, the alcohol is ethanol and the ether is diethyl ether.

The compound obtained is preferably filtered and may be purified by recrystallization, for example in an alcohol, especially isopropanol.

Preferably, the compound of formula (1) is DIMATE, a compound wherein $X^1$ and $X^2$ represent methyl. Dimate or S-methyl 4-(dimethylamino)-4-methylpent-2-ylthioate (CAS number 350229-29-7, molecular weight: 185.29 g·mol⁻¹, formula: $C_9H_{15}NOS$), is a compound of formula (IA):

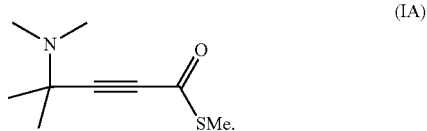

Preferably, the salt of the compound of formula (I) is dimate fumarate, the acid used in step ii) then being fumaric acid.

Preferably, step a0) corresponds to the following reaction scheme:

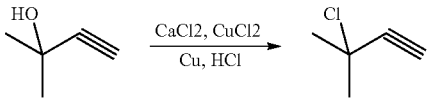

Preferably, step a1) corresponds to the following reaction scheme:

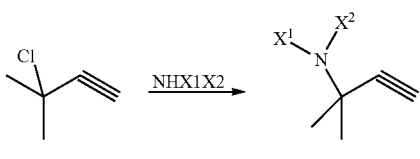

Preferably, step a) corresponds to the following reaction scheme:

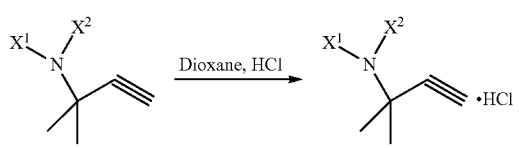

Preferably, step b) corresponds to the following reaction scheme:

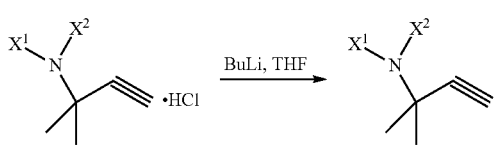

Preferably, step c) corresponds to the following reaction scheme:

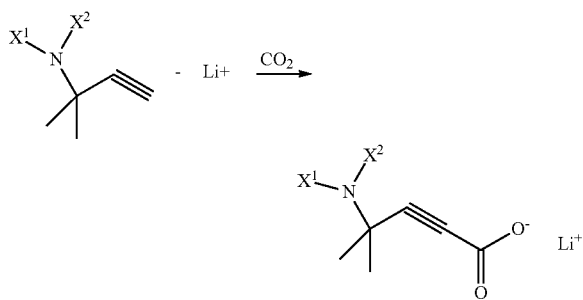

Preferably, step d) corresponds to the following reaction scheme:

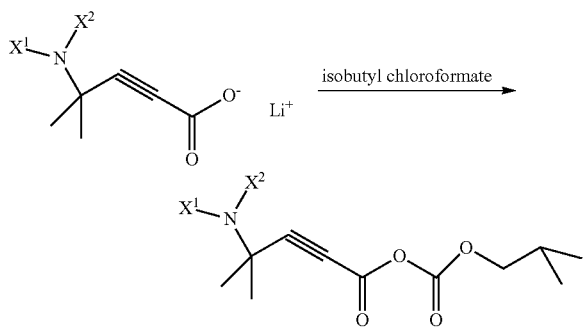

Preferably, step e) corresponds to the following reaction scheme:

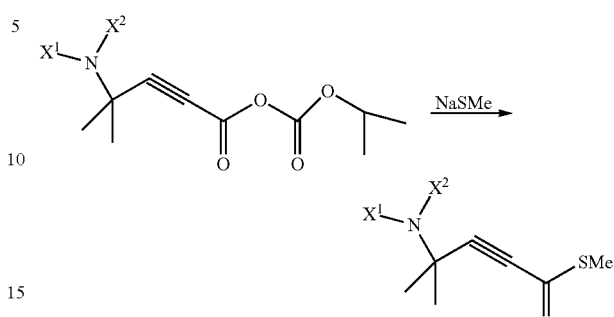

Preferably, step ii) corresponds to the following reaction scheme:

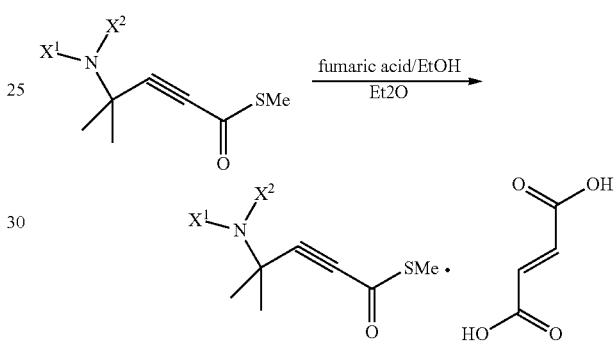

The present invention will now be described by way of non-limiting examples.

EXAMPLE 1: PREPARATION OF S-METHYL 4-(DIMETHYLAMINO)-4-METHYLPENT-2-YNETHIOATE (DIMATE) AND FUMARATE THEREOF

1. Step a0)

226.4 g of $CaCl_2$ (2.040 mol), 219.70 g of $CaCl_2$ (1.634 mol) and 2.40 g of Cu (0.0384 mol) are added to a flask. The mixture is placed at −20° C. 1770 ml of HCl (57.8 mol) are added in 30 minutes. The reaction mixture is stirred for 1 hour at −20° C. 300 g of 2-methyl-3-butyn-2-ol (4 mol) are added over 45 minutes at −20° C. After 2 h30 at −20° C. and return to room temperature (20-25° C.), the mixture is left to settle, then the phases are separated and the organic phases are washed 6 times with 140 ml of 37% HCl, then with water. The organic phases are then combined and dried over $K_2CO_3$ and then distilled over $K_2CO_3$ at 40-45° C., 350 mbar. 268 g of 3-chloro-3-methylbut-1-yne are obtained (yield 60%).

2. Step a1)

268 g of the compound obtained in step a0) (2.61 mol) are added to a flask with 476 ml of dimethylamine (40% by weight in aqueous solution) (9.41 mol). After 16 hours of reaction at room temperature, the reaction medium is filtered, the filtrate obtained is mixed and then filtered and this step is repeated 2 more times. 156.5 g of the amine are obtained (yield 53.8%).

3. Step a)

156.5 g of the amine obtained in step a1) are dissolved in 7 volumes of dioxane and 3 volumes of dioxane HCl 6.5M. At the end of the reaction at ambient temperature, the salt is filtered and washed with dioxane and then recrystallized from an EtOH/AcOEt mixture (70/30 8 volumes). 146 g of the amine salt are obtained (yield of 37.8%).

4. Stages b), c), d) and e)

500 mg of the salt obtained in step a) (0.003386 mol) is introduced, under a nitrogen atmosphere, into a flask with 5 ml of tetrahydrofuran (0.06 mol). The reaction mixture is cooled to −78° C. 3 ml of a 2.5M solution of n-BuLi in hexane are added. The reaction mixture is allowed to reach 0° C. 1 g of $CO_2$ (0.03 mol) is added (by bubbling) at 0° C. The reaction mixture is allowed to reach room temperature (20-25° C.). The reaction mixture is then cooled to 0° C. and 0.486 ml of isobutyl chloroformate (0.00372 mol) are added. The reaction mixture is allowed to reach room temperature (20-25° C.). 0.285 g of NaSMe (0.00406 mol) are added. After 20 min at room temperature (20-25° C.), water and ethyl acetate are added. The aqueous phases are extracted with ethyl acetate and the organic phases are washed with saturated NaCl solution, dried over $MgSO_4$ and concentrated to give a yellow oil (600 mg). The product obtained is purified on silica gel with a 9/1 to 7/3 cyclohexane/AcOEt eluent and the dimate is obtained (157 mg) in the form of a colorless oil (yield 25.02%).

5. Step ii)

11.4 g of fumaric acid (0.09821 mol) are dissolved in 450 ml of ethanol (7.7 mol) at room temperature, a sonication that may achieve total solubilization. This solution is added dropwise to a solution of 19.2 g of dimate (0.1036 mol) in 250 ml of ether (2.4 mol). After 30 minutes, the resulting mixture is filtered, washed with ether (50 ml), dried under vacuum and the dimate fumarate is obtained as a white solid (19.1 g, 64.5% yield).

Compound Obtained at the End of Step e) (DIMATE)

$^1$H NMR (300 MHz, $CDCl_3$): δ=1.42 (s, 6H, $(CH_3)_2$), 2.31 (s, 6H, $N(CH_3)_2$), 2.39 ppm (s, 3H, $CH_3S$).

$^1$H NMR (300 MHz, DMSO-$d_6$): δ=1.35 (s, 6H, $(CH_3)_2$), 2.20 (s, 6H, N(CH3h), 2.39 ppm (s, 3H, CH3S).

$^{13}$C NMR (75 MHz, $CDCl_3$): 0=12.1 ($CH_3S$) −27.5 $((CH_3)_2)$, 40.0 ($N(CH_3)_2$), 54.7 (C), 81.5 (C), 94.7 (C), 175.8 (COS) ppm Compound Obtained at the End of Step ii) (DIMATE FUMARATE):

$^1$H NMR (300 MHz, DMSO-$d_6$): δ=1.36 (s, 6H, $(CH_3)_2$), 2.21 (s, 6H, $N(CH_3)_2$), 2.39 (s, 3H, $CH_3S$), 6.63 (s, 2H, =CH), 13.12 ppm (s, 2H, $CO_2H$).

$^1$H NMR (300 MHz, $D_2O$): δ=1.79 (s, 6H, $(CH_3)_2$), 2.46 (s, 3H, $CH_3S$), 2.98 (s, 6H, $N(CH_3)_2$), 6.68 ppm (s, 2H, =CH).

$^{13}$C NMR (75 MHz, DMSO-$d_6$): δ=12.3 ($CH_3S$), 27.2 $((CH_3)_2)$, 39.8 ($N(CH_3)_2$), 54.7 (C), 81.2 (C), 95.4 (C), 134.1 (=CH), 166.1 ($CO_2H$), 175.8 (COS) ppm

EXAMPLE 2: PREPARATION OF S-METHYL-4-[HEPTYL (METHYL) AMINO]-4-METHYL-PENT-2-YNETHIOATE

The procedure detailed in steps a0) to e) is repeated using the following amine (compound of formula II): N-(1,1-dimethylprop-2-ynyl)-N-methyl-heptan-1-amine. To N-methylheptan-1-amine (3.84 g, 29.7 mmol) dissolved in THF (50 mL) are added successively at room temperature (20-25° C.) diisopropylamine (4.3 mL, 24.7 mmol), Cu (0.150 g, 2.4 mmol), CuCl (0.150 g, 1.5 mmol) and then 3-chloro-3-methylbut-1-yne (2.54 g, 24.8 mmol) (obtained as mentioned in Example 1). The reaction medium is stirred for 16 hours. After addition of 25 mL of water and decantation, the aqueous phase is extracted with ethyl acetate (3×30 mL). The combined organic phases are washed successively with 10% aqueous $NH_4OH$ (25 mL) and a saturated aqueous solution of NaCl (25 mL). After drying over $Na_2SO_4$, concentration on a rotary evaporator, the residue is purified by vacuum distillation in a Kugelrohr apparatus (18 Torr, oven temperature: 100 to 150° C.). 2.10 g of N-(1,1-dimethylprop-2-ynyl)-N-methyl-heptan-1-amine are obtained in the form of a colorless oil, yield 43%.

Molecular weight=195.35

Chemical formula=C13H25N.

$^1$H NMR (300 MHz, DMSO) δ 3.08 (s, 1H), 2.37-2.28 (m, 2H), 2.13 (s, 3H), 1.39-1.18 (m, 10H), 1.27 (s, 6H), 0.91-0.80 (m, 3H).

$^{13}$C NMR (75 MHz, $CDCl_3$) δ 086.29 (C), 70.72 (CH), 54.59 (C), 52.36 ($CH_2$), 36.27 ($CH_3$), 31.95 ($CH_2$, 29.36 ($CH_2$), 29.05 ($CH_2$), 28.49 ($CH_3$)), 27.61 ($CH_2$), 22.69 ($CH_2$), 14.14 ($CH_3$).

ESI-LRMS 196.0 [M+H]$^+$.

The final product is obtained from 0.51 g (2.6 mmol) of N-(1,1-dimethylprop-2-ynyl)-N-methyl-heptan-1-amine with a yield of 25% in liquid form (free base) (0.176 g)

Compound Obtained at the End of Step e) (S-methyl 4-[heptyl(methyl) amino]-4-methyl-pent-2-ynethioate)

$^1$H NMR (300 MHz, DMSO) δ 2.38 (s, 3H), 2.37 (t, J=7.0 Hz, 2H), 2.18 (s, 3H), 1.35 (s, 6H), 1.42-1.20 (m, 10H), 0.86 (t, J=6.7 Hz, 3H).

$^{13}$C NMR (75 MHz, $CDCl_3$) δ 176.38 (C), 96.50 (C), 81.03 (C), 54.98 (C), 52.39 ($CH_2$), 36.39, 31.85 ($CH_2$), 29.25 ($CH_2$), 28.79 ($CH_2$), 27.81 ($2CH_3$), 27.41 ($CH_2$), 22.62 ($CH_2$), 14.09 ($CH_3$), 12.41 ($CH_3$).

ESI-LRMS 270.2 [M+H]$^+$.

EXAMPLE 3 PREPARATION OF S-METHYL 4-(DIHEPTYLAMINO)-4-METHYL-PENT-2-YNETHIOATE

The method detailed in steps a0) to e) is repeated using the following amine (compound of formula II): N-(1,1-dimethylprop-2-ynyl)-N-heptyl-heptan-1-amine.

To N-heptylheptan-1-amine (5.2 g, 24.4 mmol) dissolved in THF (41 mL) are added successively at room temperature (20-25° C.) diisopropylamine (3.54 mL, 20.3 mmol), Cu (0.120 g, 1.9 mmol), CuCl (0.120 g, 1.2 mmol) then 3-chloro-3-methylbut-1-yne (2.08 g, 20.3 mmol)) (obtained as mentioned in Example 1). The reaction medium is stirred for 16 hours. After addition of 25 mL of water and decantation, the aqueous phase is extracted with ethyl acetate (3×30 mL). The combined organic phases are washed successively with 10% aqueous $NH_4OH$ (25 mL) and a saturated aqueous solution of NaCl (25 mL). After drying over $Na_2SO_4$, concentration on a rotary evaporator, the residue is purified by vacuum distillation in a Kugelrohr apparatus (18 Torr, oven temperature: 100 to 150° C.). 1.50 g of N-(1,1-dimethylprop-2-ynyl)-N-heptyl-heptan-1-amine are obtained in the form of a colorless oil, yield 27%.

The final product is obtained from 0.51 g (1.82 mmol) of N-(1,1-dimethylprop-2-ynyl)-N-heptyl-heptan-1-amine with a yield of 29% in the form of a liquid (base free) (0.187 g).

Compound Obtained at the End of Step e) (S-methyl 4-(diheptylamino)-4-methyl-pent-2-ynethioate)

$^{13}$C NMR (75 MHz, $CDCl_3$) δ 176.50 (C), 98.81 (C), 80.18 (C), 54.80 (C), 51.21 ($CH_2$), 31.94 ($CH_2$), 30.05

($CH_2$), 29.29 ($CH_2$), 28.61 ($CH_3$), 27.45 ($CH_2$), 22.67 ($CH_2$), 14.13 ($CH_3$), 12.41 ($CH_3$).

ESI-LRMS 354.1 $[M+H]^+$.

or compound.

The invention claimed is:

1. A method for the preparation of compounds of formula (1)

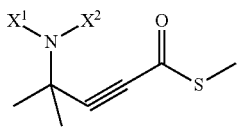

(I)

in which $X^1$ and $X^2$, which are identical or different, are chosen from $C_1$ to $C_7$ alkyls, phenyl, benzyl, or $X^1$ and $X^2$ form with the nitrogen atom, which carries them, a heterocycle wherein the method comprises the following steps:

a) reaction of a compound of formula (II) with an inorganic acid or an organic acid

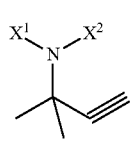

(II)

b) reaction of the compound obtained in step a) with a base;
c) reaction of the compound obtained in step b) with $CO_2$;
d) reaction of the compound obtained in step c) with an alkyl chloroformate, a reagent capable of forming, with the compound obtained in step c), an acid halide or a reagent capable of forming, with the compound obtained in step c), a mixed anhydride; and
e) reaction of the compound obtained in step d) with an $SMe^-$ anion precursor compound.

2. The method according to claim 1, wherein the compound of formula (II) is obtained by a step a1) of reaction of 3-chloro-3-methylbut-1-yne with $X^1X^2NH$ in an aqueous medium.

3. The method according to claim 2, wherein the compound obtained in step a1) is purified by one or more filtrations.

4. The method according to claim 2, wherein the 3-chloro-3-methylbut-1-yne is obtained by a step a0) of reaction of 2-methylbut-3-yn-2-ol with hydrochloric acid in the presence of a copper catalyst.

5. The method according to claim 1, wherein the inorganic acid is selected from the group consisting of hydrochloric acid, phosphoric acid, nitric acid, and sulfuric acid.

6. The method according to claim 1, wherein the base of step b) has a pKa greater than 25.

7. The method according to claim 1, wherein step d) is implemented with:
an alkyl chloroformate having a 1-6 carbon alkyl, which may comprise at least one double bond; or
a reagent capable of forming with the compound obtained in stage c) a mixed anhydride chosen from acid chlorides; or
a reagent capable of forming with the compound obtained in stage c) an acid halide selected from the group consisting of $SOCl_2$, $COCl_2$, $PCl_3$, $PCl_5$, $PBr_3$ and $PPh_3Br_2$.

8. The method according to claim 1, wherein the $SMe^-$ anion precursor compounds are selected from the group consisting of salts of formula XSMe, wherein X represents an alkali metal or alkaline earth metal, the methyl mercaptan, and $(SMe)_2$.

9. The method for preparing a salt of a compound of formula (1) as described in claim 1, comprising the steps of:
i) preparation of the compound of formula (1) according to the method of claim 1;
ii) reaction of the compound obtained in step i) with the acid corresponding to the desired salt.

10. The method according to claim 1, wherein $X^1$ or $X^2$, which are identical, represent a methyl.

11. The method according to claim 9, wherein said salt is fumaric, wherein said compound of formula (1) has $X^1$ and $X^2$, identical, representing a methyl, and in which the acid used in step ii) is fumaric acid.

12. The method according to claim 6, wherein the base implemented in step b) is chosen from bases based on lithium or magnesium.

13. The method according to claim 8, wherein the alkyl chloroformate is selected from the group consisting of methyl, ethyl, isoprenyl, isobutyl or isobutyl chloroformate.

14. The method according to claim 3, wherein the compound obtained in step a1) is purified in a succession of 2 to 10 filtrations.

15. The method according to claim 5, wherein the acid is hydrochloric acid.

16. The method according to claim 7, wherein the reagent capable of forming with the compound obtained in stage c) is pivaloyl chloride.

17. The method according to claim 12, wherein the base implemented in step b) is butyllithium or hexyllithium.

18. The method according to claim 13, wherein the alkyl chloroformate is isobutyl chloroformate.

19. The method according to claim 8, wherein the $SMe^-$ anion precursor compound is NaSMe.

* * * * *